US006291198B1

(12) United States Patent
Uchida et al.

(10) Patent No.: US 6,291,198 B1
(45) Date of Patent: Sep. 18, 2001

(54) ANTIBODY THAT RECOGNIZES PYRAZINE DERIVATIVE AND METHOD FOR MEASURING 1,2-DICARBONYL DERIVATIVE USING SAID ANTIBODY

(75) Inventors: Yoshiaki Uchida; Yoshihiro Kurano; Satoru Ito, all of Tokyo (JP)

(73) Assignee: The Fujirebio Inc., Tokyo (JP)

( * ) Notice: Subject to any disclaimer, the term of this patent is extended or adjusted under 35 U.S.C. 154(b) by 0 days.

(21) Appl. No.: 09/134,388

(22) Filed: Aug. 14, 1998

(30) Foreign Application Priority Data

Aug. 21, 1997 (JP) .................................... 9-240348

(51) Int. Cl.[7] .................. G01N 33/545; G01N 33/64; C07K 16/44
(52) U.S. Cl. .................. 435/7.94; 435/7.5; 530/388.9; 530/389.8; 530/391.1; 530/391.3; 530/404; 530/405; 530/807
(58) Field of Search ............... 530/388.9, 389.8, 530/391.3, 391.1, 404, 405, 807; 435/7.5, 7.94

(56) References Cited

PUBLICATIONS

Kevin J. Knecht et al.; "Detection of 3–Deoxyfructose and 3–Deoxyglucosone in Human Urine and Plasma: Evidence for Intermediate Stages of the Maillard Reaction in Vivo[1]"; Archives of Biochemistry and Biophysics; vol. 294, No. 1, 1992, pp.130–137.

Toshimitsu Niwa et al.;"Presence of 3–Deoxyglucosone, A Potent Protein Crosslinking Intermediate of Maillard Reaction, In Diabetic Serum"; Biochemical and Biophysical Research Communications; vol. 196, No. 2, 1993, pp. 837–843.

Hiroyuki Yamada et al.; "Increase in 3–Deoxyglucosone Levels in Diabetic Rat Plasma"; The Journal of Biological Chemistry; vol. 269, No. 32, 1994, pp. 20275–20280.

Ei Fujji et al.; "Quantitation of the Glycation Intermediate 3–Deoxyglucosone By Oxidation with Rabbit Liver Oxoaldehyde Dehydrogenase to 2–Keto–3–Deoxygluconic Acid Followed By High–Performance Liquid Chromatography"; Journal of Chromatography B; vol. 660, 1994, pp. 265–270.

Toshimitsu Niwa et al.; "Elevated Serum Levels of 3–Deoxyglucosone, a Potent Protein–Cross–Linking Intermediate of the Maillard Reaction, in Uremic Patients"; NEPHRON; vol. 69, 1995, pp. 438–443.

Sundeep Lal et al.; "Quantitation of 3–Deoxyglucosone Levels in Human Plasma"; Archives of Biochemistry and Biophysics; vol. 342, No. 2, 1997, pp. 254–260.

Naoyuki Taniguchi et al.; "Involvement of Glycation and Oxidative Stress in Diabetic Macroangiopathy"; Diabetes; vol. 45, Sp3, 1996, s81–83.

Chemical Abstracts, vol. 118, 1993, Reference 231710.

*Primary Examiner*—Mary E. Ceperley
(74) *Attorney, Agent, or Firm*—Banner & Witcoff, LTD

(57) ABSTRACT

A method for simply measuring a 1,2-dicarbonyl derivative in multiple specimens is provided, which comprises converting a 1,2-dicarbonyl derivative to a pyrazine derivative represented by the formula (I):

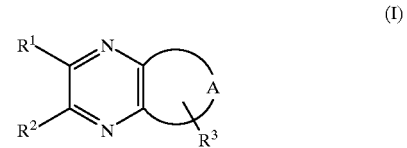

(I)

wherein $R^1$ and $R^2$ independently represent a hydrogen atom, a methyl group, a hydroxymethyl group, a hydroxyethyl group, a dihydroxyethyl group, a dihydroxypropyl group, a trihydroxypropyl group, or a trihydroxybutyl group, A represents a group that binds to the pyrazine ring to form a 6-membered aromatic hydrocarbon group, a 5- or 6-membered aromatic heterocyclic group, or a 5- or 6-membered alicyclic hydrocarbon group, and $R^3$ represents a linking residue, wherein said 5-membered ring formed by A may have 1 or 2 substituents and said 6-membered ring may have 1 to 3 substituents, in addition to $R^3$ and measuring the pyrazine derivative by an immunological method using an antibody that recognizes the pyrazine derivative.

32 Claims, 5 Drawing Sheets

ANTIBODY THAT RECOGNIZES PYRAZINE DERIVATIVE AND METHOD FOR MEASURING 1,2-DICARBONYL DERIVATIVE USING SAID ANTIBODY

FIELD OF THE INVENTION

The present invention relates to an antibody recognizing a pyrazine derivative, which is a reaction product of a 1,2-dicarbonyl derivatives that is an intermediate of advanced glycated protein in vivo, an immunogen that induces said antibody, and a method for immunological assay of a 1,2-dicarbonyl derivative using said antibody.

BACKGROUND OF THE INVENTION

Diabetes is a metabolic disease attributed to insulin and produces various kinds of complications, including, for example, eye diseases, kidney diseases, neurological disorders, cardiovascular complications, and gangrenes, since it is liable to become chronic. Prognosis of the patients is greatly influenced by the presence or absence and the degree of complications.

Deoxyglucosone is an intermediate produced in glycation of protein, which is suspected to be the potent cause of diabetes, and serves as a cross-linker between proteins to enhance production of an advanced glycated end proteins. This substance has attracted attention as an index for assessment of symptoms of diabetic complications from the facts that its blood level increased in patients with diabetes who are likely to maintain hyperglycemic conditions, especially patients with diabetes complicated with kidney diseases (Biochem. Biophys. Res. Commun. 196, 837–843, 1993) and patients with diabetic arteriosclerosis (DIABETES, 45, SP3, S81–83, 1996). It has also been suggested that the methylglyoxal blood level increased in patients with diabetic arteriosclerosis (DIABETES, 45, SP3, S81–83, 1996). Accordingly, attention has been paid to behavior of 1,2-dicarbonyl derivatives in cases of diabetes.

However, since 1,2-dicarbonyl derivatives, represented by deoxyglucosone, are very reactive, the compounds have been so far determined by converting them to derivatives or stable forms, extracting the conversion products, and measuring the products by chromatographic analysis such as GS/MS, HPLC, or the like. In such a method, operation of extracting 1,2-dicarbonyl derivatives and procedures for chromatographic analysis are complicated and time-consuming. Therefore, it has been desired to develop a simple method for measuring 1,2-dicarbonyl derivatives in multiple specimens.

SUMMARY OF THE INVENTION

An object of the present invention is to provide a simple method for measuring 1,2-dicarbonyl derivatives in multiple specimens. Another object of the present invention is to provide antibodies to be used in the above method, and immunogens that induce the production of the antibodies.

As a result of intensive studies, the present inventors found that a 1,2-dicarbonyl derivative in a specimen could be measured by reacting the 1,2-dicarbonyl derivative with a diamino derivative to convert it to a stable pyrazine derivative and measuring the pyrazine derivative by an immunological assay using an antibody that recognizes the pyrazine derivative. The present inventors succeeded to provide the above antibody and, thus, the present invention was completed.

The present invention provides an antibody that recognizes at least a region comprising $R^1$, $R^2$, carbon atoms in the pyrazine ring to which $R^1$ and $R^2$ are respectively attached, and nitrogen atoms in the pyrazine ring attached to said carbon atoms, of a pyrazine derivative represented by the formula (I):

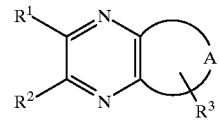

(I)

wherein $R^1$ and $R^2$ independently represent a hydrogen atom, a methyl group, a hydroxymethyl group, a hydroxyethyl group, a dihydroxyethyl group, a dihydroxypropyl group, a trihydroxypropyl group, or a trihydroxybutyl group, A represents a group that binds to the pyrazine ring to form a 6-membered aromatic hydrocarbon group, a 5- or 6-membered aromatic heterocyclic ring group, or a 5- or 6-membered alicyclic hydrocarbon group, and $R^3$ represents a linking residue, where said 5-membered ring formed by A may have 1 or 2 substituents and said 6-membered ring may have 1 to 3 substituents, in addition to $R^3$.

The present invention also provides an immunogen comprising the pyrazine derivative represented by the formula (I) or the pyrazine derivative to which a carrier is bound via $R^3$.

The present invention further provides a method for measuring 1,2-dicarbonyl derivative, which is an intermediate of glycation in vivo, by an immunological assay, comprising the steps of:

reacting a 1,2-dicarbonyl derivative in a specimen with a diamino derivative represented by the formula (II):

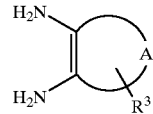

(II)

wherein $R^3$ and A are as defined in the formula (I), to produce a pyrazine derivative represented by the formula (I); and measuring the pyrazine derivative by an immunological assay utilizing the antigen-antibody reaction between the pyrazine derivative and the above antibody according to the present invention to thereby measure the 1,2-dicarbonyl derivative in the specimen.

Furthermore, the present invention provides a kit for immunological determination of 1,2-dicarbonyl derivative, comprising the antibody as described above and the diamino derivative represented by the formula(II).

DETAILED DESCRIPTION OF THE INVENTION

Figure 1:
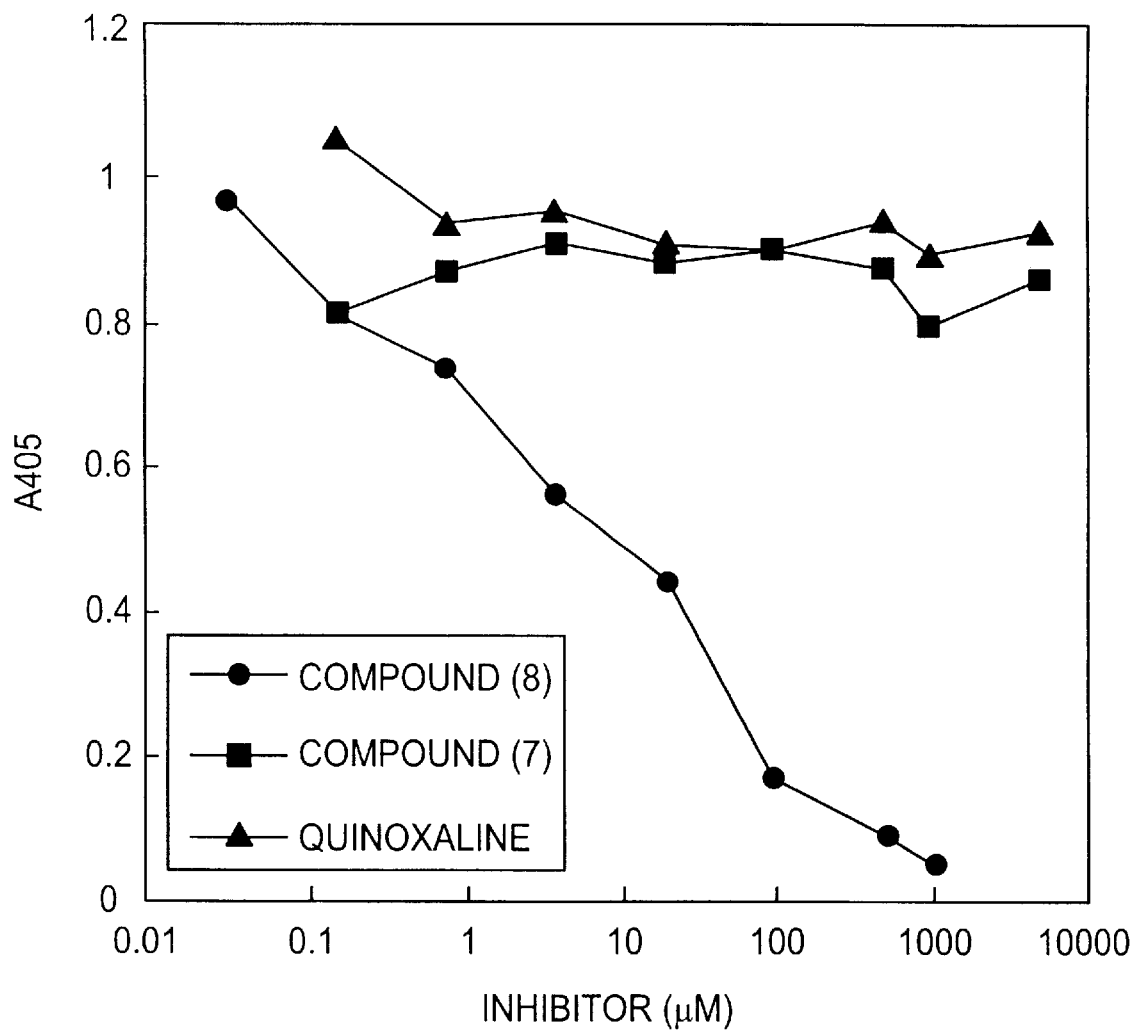
FIG. 1 illustrates the reaction specificity of anti-pyrazine derivative monoclonal antibody 3DG-451 to BSA-bound pyrazine derivatives derived from fraction (A) (plate A) obtained in Example 3.

The antibody of the present invention recognizes the pyrazine derivative represented by the above formula (I).

The definition of in the formula (I) is as described above. Preferable combination of $R^1$ and $R^2$ includes hydrogen as $R^1$ and trihydroxybutyl as $R^2$, methyl as $R^1$ and trihydroxypropyl as $R^2$, or hydroxymethyl as $R^1$ and dihydroxypropyl as $R^2$.

The definition of A in the formula (I) is as described above. The ring formed by A is preferably pyridine, benzene, furan, or thiophene. The ring formed by A may have any 1 or 2 substituents when the ring is a 5-membered ring and 1 to 3 substituents when the ring is a 6-membered ring, in addition to $R^3$. Examples of these substituents include a carboxyl group; a sulfonyl group; an alkoxycarbonyl group; a carbamoyl group; a cyano group; a formyl group; a hydroxyl group; a mercapto group; a nitro group; a halogen atom; an aromatic hydrocarbon group, an aromatic heterocyclic group, and an aliphatic hydrocarbon group, each of which may be substituted with a carboxyl group, a sulfonyl group, an alkoxycarbonyl group, a carbamoyl group, a cyano group, a formyl group, a hydroxyl group, a mercapto group, a nitro group, or a halogen atom. The hydrocarbon chain of the above aliphatic hydrocarbon group may be substituted with an oxygen atom or a sulfur atom.

$R^3$ in the formula (I) represents a linking residue. The term "linking residue" used herein means the chemical structure capable of binding a pyrazine derivative to the other substance. $R^3$ may have any specific chemical structure as long as it serves to bind a pyrazine residue to a carrier or the other substance such as a label. Accordingly, the bond formed by the linking residue may be either covalent bond or noncovalent bond. The noncovalent bond includes, for example, a hydrophobic bond, a hydrogen bond, an ionic bond, and a coordinate bond. Specific examples thereof includes a long-chain aliphatic hydrocarbon (preferably having 8–18 carbon atoms), a carboxylate ion, an ammonium ion, etc. In the case of the covalent bond, $R^3$ preferably comprises a spacer portion and a reactive portion. The reactive portion means a functional group that can react with other compounds and form the covalent bond, including, for example, a carboxyl group, a hydroxyl group, a sulfhydryl group, an amino group, a maleimide group, an aldehyde group, a halogen atom, and derivatives of these functional groups activated to bind to the other compounds. The spacer portion means a chemical structure that can make suitable space between the pyrazine residue and the reactive portion, including, for example, an aliphatic hydrocarbon (preferably having 2–6 carbon atoms), an aromatic hydrocarbon, or a structure produced by binding these compounds via an ester bond, an amide bond, an ether bond, a thioether bond, a disulfide bond, or a Schiff base bond. $R^3$ may have only the reactive portion without any spacer portion.

The linking residue represented by $R^3$ is capable of binding a pyrazine derivative to the other substances directly or indirectly mediated by a reactive bivalent linking agent.

Examples of the reactive bivalent linking agent include N-succinimidyl-3-[2-pyridyldithio]propionate (SPDP), N-γ-maleimidobutyryloxysuccinimide ester (GMBS), 1-ethyl-3-[3-dimethylaminopropyl]carbodiimide hydrochloride (EDC), N,N'-dicyclohexylcarbodiimide (DCC), 3-[2-pyridyldithio]propionyl hydrazide (PDPH), and 4-(4-N-maleimidomethyl)butyric acid hydrazide HCl (MPBH).

The preferable pyrazine derivative of the present invention is the compound of the formula (I) in which one of $R^1$ and $R^2$ is a hydrogen atom and the other is a 2,3,4-trihydroxybutyl group, A is benzene, and $R^3$ is a 4-carboxamidobutanoyl-(2-mercapto)ethylamido group, that is N-(4-(3-(2,3,4-trihydroxybutyl)quinoxaline-6-carboxamido)-butanoyl)- 2-mercaptoethylamine or N-(4-(2-(2,3,4-trihydroxybutyl)-quinoxaline-6-carboxamido) butanoyl)-2-mercaptoethylamine. The chemical structures of N-(4-(3-(2,3,4-trihydroxybutyl)-quinoxaline-6-carboxamido)butanoyl)-2-mercaptoethylamine and N-(4-(2-(2,3,4-trihydroxybutyl)quinoxaline-6-carboxamido)-butanoyl)-2-mercaptoethylamine are shown below.

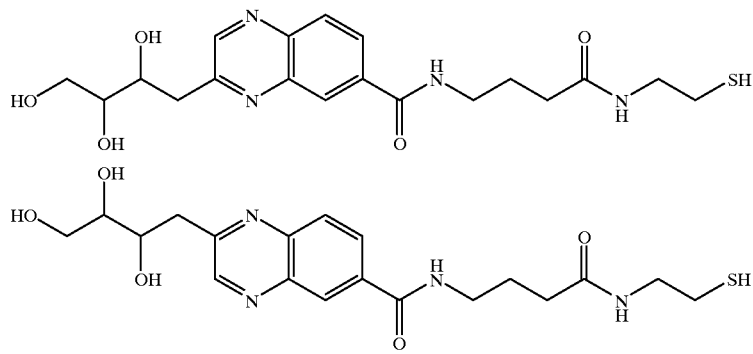

The antibody of the present invention recognizes the above-described pyrazine derivative, especially at least the region comprising $R^1$, $R^2$, carbon atoms in the pyrazine ring to which $R^1$ and $R^2$ are respectively attached, and nitrogen atoms in the pyrazine ring attached to said carbon atoms, of the derivative. As will be described in more detail later, the antibody of the present invention is used to measure a 1,2-dicarbonyl derivative in a specimen. The 1,2-dicarbonyl derivative reacts with a diamino derivative as described below to form the pyrazine derivative represented by the formula (I). The thus-formed pyrazine derivative is measured using the antibody of the present invention. The 1,2-dicarbonyl derivative constitutes the pyrazine residue in the pyrazine derivative, to which $R^1$, $R^2$, and substituents thereof are bound. Accordingly, the antibody of the present invention must recognize at least the region including $R^1$ or $R^2$ of the pyrazine derivative. For example, an antibody that recognizes only $R^3$ cannot be the antibody of present invention. Needless to say, an antibody that recognizes the pyrazine derivative as a whole inclusive of $R^3$ is included in the antibody of the present invention.

The antibody of the present invention may be either polyclonal or monoclonal though a monoclonal antibody is preferable since antibodies with the same reaction specificity can be obtained with good reproducibility. Polyclonal antibody may contain the antibodies that recognize the regions other than those including $R^1$ or $R^2$ of the pyrazine derivative.

The antibody of the present invention can be prepared using the ordinary method using as an immunogen the pyrazine derivative of the formula (I) or the pyrazine derivative, to which an carrier is bound via $R^3$. The latter derivative with the carrier is preferably used. As the carrier, it is preferable to use protein such as bovine serum albumin (BSA) or keyhole lympet hemocyanin (KLH).

In the case of polyclonal antibody, the antibody of the present invention can be obtained by immunizing an animal with the above immunogen and preparing antibodies from antiserum by the ordinary method.

The monoclonal antibody can be prepared by the ordinary method. Namely, hybridomas are produced by fusion of the antibody-producing cells such as spleen cells of the animal immunized with the above immunogen with tumor cells such as myeloma cells using a fusion accelerator such as polyethylene glycol, etc. Then, hybridomas are selected to clone in single colonies using a selection medium such as a HAT medium and cultured by the limiting dilution method and the like suitable method. The culture supernatant is subjected to an appropriate immunological assay such as enzyme immunoassay to select clones producing the desired anti-pyrazine derivative antibody. This procedure for production of monoclonal antibodies can be carried out using the known method such as the method of Kohler and Milstein (Nature256:495, 1975)or the method of Scherrer (Nature285:446,1980). Monoclonal antibodies prepared by the above method can be recovered from the culture supernatant using the conventional purification methods including salting-out, ion-exchange chromatography, gel filtration, and the like.

The antibody recognizing the regions other than comprising at least $R^1$, $R^2$, carbon atoms in the pyrazine ring to which $R^1$ and $R^2$ are respectively attached, and nitrogen atoms in the pyrazine ring attached to said carbon atoms, of the pyrazine derivative can be obtained by measuring the 1,2-dicarbonyl derivative using the antibody according to the method of present invention as described below with varying concentrations of the 1,2-dicarbonyl derivative to prepare the calibration curve and selecting the antibody that produces the calibration curve varies depending on the concentration of the 1,2-dicarbonyl derivative.

The method for measuring a 1,2-dicarbonyl derivative using the antibody of the present invention will be described below.

The 1,2-dicarbonyl derivatives to be assayed by the method of the present invention are those produced as intermediates in glycation of proteins in vivo, including 2-deoxyglucosone, 3-deoxyglucosone, 4-deoxyglucosone, methylglyoxal, etc.

The specimen containing 1,2-dicarbonyl derivatives are usually exemplified by body fluids such as serum, plasma, blood, or urine, and biological tissues though it is not limited thereto.

According to the method of the present invention, a 1,2-dicarbonyl derivative in a specimen is reacted with the diamino derivative of the formula (II) to produce the pyrazine derivative of the formula (I). The reaction can be carried out by simply mixing the specimen with the diamino derivative at preferably 4 to 37° C., more preferably room temperature for preferably about 12 to 20 hours. The concentration of the diamino derivative to be used in the reaction ranges usually from about 1 to about 50 µg/ml, preferably about 5 to about 20 µg/ml. The reaction between the 1,2-dicarbonyl derivative and the diamino derivative may be carried out either before or simultaneously with the immunological reaction. The reaction scheme of 3-deoxyglucosone, which is an example of the 1,2-dicarbonyl derivative, with a diaminobenzene derivative, which is an example of the diamino derivative, is shown below.

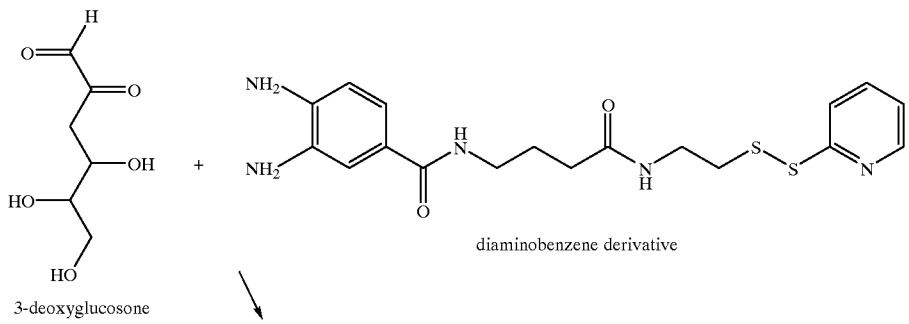

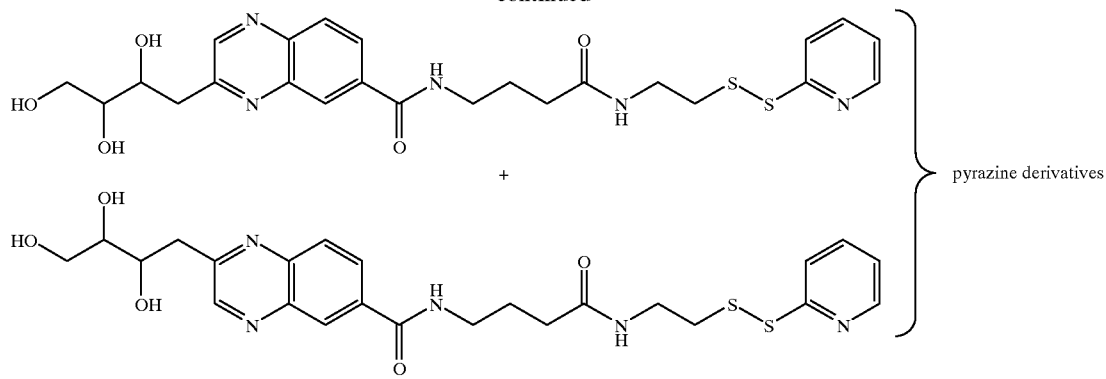

Then, the pyrazine derivative represented by the formula (I) formed by the above reaction is measured by the immunological assay using the antibody of the present invention. Any method among the immunological assays per se well known in the art can be used in the present invention as long as the methods utilize the immunological reaction between the antibody and the pyrazine derivative. Such methods include immunohistochemical staining, immunonephelometry, radioimmunoassay, enzyme immunoassay, etc.

In a preferable example of the immunological measuring method, $R^3$ of the diamino derivative is labeled with a detectable label and the immunological assay is carried out by binding the antibody of the present invention to a solid phase, reacting the antibody bound to the solid phase with the pyrazine derivative, washing the reaction product, and measuring the pyrazine derivative in terms of the amount of the label bound to the solid phase. In this method, any label ordinarily used in the art can be used, including biotin, enzyme, radioactive isotopes, or the like.

The kit of the present invention comprises the above-described antibody of the present invention and the diamino derivative. The antibody is preferably immobilized on a solid carrier for use in immunoreaction, such as an ELISA plate, beads, or magnetic particles, by a covalent bond or physical adsorption. Alternatively, the kit may contain the antibody that is not immobilized and a substance immobilized on a solid phase, to which the antibody binds to be indirectly immobilized on the solid phase. In this case, the combination of the antibody and the immobilized substance may be the antibody of the present invention and an immobilized anti-mouse globulin or the biotinized antibody of the present invention and an immobilized avidin. The diamino derivative included in the kit is preferably labeled with, for example, an enzyme, a radioisotope (RI), a fluorescent substance, through A or $R^3$ of the formula (II). Alternatively, the kit may contain the diamino derivative that is not labeled and a labeled substance, to which the diamino derivative binds to be indirectly labeled. In this case, the combination of the diamino derivative and the labeled substance may be the biotinized diamino derivative and avidin labeled with an enzyme, RI, or a fluorescent substance or the diamino derivative and a labeled antibody where the diamino derivative has the antibody-recognition site. The diamino derivative included in the kit may be in the liquid or lyophilized form. When the derivative is lyophilized, the kit may also contain a solution for reconstitution.

The kit may further comprise the other reagents such as the standard 1,2-dicarbonyl derivative solution with a predetermined concentration, which may be in the liquid or lyophilized form. When the label used is an enzyme, a corresponding substrate and a reaction-terminating solution can be contained. When the label used is a fluorescent substance, a buffer to cause fluorescence can be contained.

The present invention provides antibody to be used in measurement of 1,2-dicarbonyl derivatives as an index of diabetic complications. The method utilizing the antibody according to the present invention enables a simple assay of 1,2-dicarbonyl derivatives.

The present invention will be described in detail with reference to the following Examples, but is not construed to be limited thereto.

REFERENCE EXAMPLE 1

Synthesis of N-t-butoxycarbonyl-4-aminobutyric acid (Compound (1))

4-Aminobutyric acid (5.16 g) was dissolved in 20 ml of water. To the resulting solution were added 8.4 ml of N-methylmorpholine and 11.08 g of 2-t-butoxycarbonyloxyimino-2-phenylacetonitrile in 50 ml of acetone. After stirring the resulting mixture overnight at room temperature, about a half of the solvent was distilled off. Water and ethyl acetate were added thereto and thoroughly mixed to separate the solution. The aqueous phase was washed with ethyl acetate, combined with the organic phase, and extracted with 5% aqueous sodium hydrogencarbonate. After combining the aqueous phases, ethyl acetate was added thereto and the pH was adjusted to about 3 with 6 N hydrochloric acid to separate the solution. The aqueous phase was extracted twice with ethyl acetate. The extracts were combined, washed with water, and dried over anhydrous magnesium sulfate. After removal of the desiccant, N,N-dicyclohexylamine was added thereto for crystallization. Crystals were collected by filtration, washed with ether, and dried to obtain 15.07 g of an N,N-dicyclohexylamine salt (yield 79%).

The whole amount of the N,N-dicyclohexylamine salt was dissolved in a mixed solution of ethyl acetate and 5% aqueous citric acid and the mixture was separated. The aqueous phase was extracted with ethyl acetate. The organic phases were combined, washed with 5% aqueous citric acid and water, and dried over anhydrous magnesium sulfate. The solvent was distilled off to obtain 7.57 g of N-t-butoxycarbonyl-4-aminobutyric acid (hereinafter referred to as Compound (1)) as oil. The chemical formula of Compound (1) is shown below. In the formula, Boc represents a t-butoxycarbonyl group.

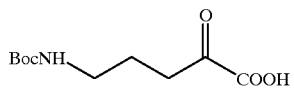

Compound (1)

The NMR data of Compound (1) are as follows.
$^1$H-NMR (400 MHz, CDCl$_3$, ppm) δ 1.44 (9H, s), 1.82 (2H, m, J=7.0, 7.0 Hz), 2.40 (2H, t, J=7.0 Hz), 3.18 (2H, m), 4.72 (1H, s).

REFERENCE EXAMPLE 2

Synthesis of S-(2-pyridylthio)-2-mercaptoethylamine hydrochloride (Compound (2))

2,2'-dipyridyldisulfide (13.2 g) was dissolved in 100 ml of methanol. Under vigorously stirring, 3.4 g of 2-mercaptoethylamine hydrochloride in 30 ml of methanol was added dropwise thereto. The reaction mixture was stirred for 1 hour and 40 minutes and the solvent was distilled off. Ethyl acetate was added to the resulting residue for crystallization and crystals were collected by filtration. Crude crystals thus obtained were recrystallized from methanol-ether. The mother liquor was concentrated and crystallized again from ether to obtain 5.62 g of S-(2-pyridylthio)-2-mercaptoethylamine hydrochloride (hereinafter referred to as Compound (2)) (yield 84%). The chemical formula of Compound (2) is shown below.

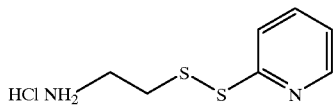

Compound (2)

The NMR data of Compound (2) are as follows.
$^1$H-NMR (400 MHz, DMSO-D$_6$, ppm) δ 3.09 (4H, m), 7.30 (1H, m, J=1.1, 4.8, 7.4 Hz), 7.75 (1H, m, J=0.9, 1.1, 8.0 Hz), 7.84 (1H, m, J=1.8, 7.4, 8.0 Hz), 8.10 (3H, s), 8.52 (1H, m, J=0.9, 1.8, 4.8 Hz).

REFERENCE EXAMPLE 3

Synthesis of N-(4-t-butoxycarboxamidobutanoyl)-S-(2-pyridylthio)-2-mercaptoethylamine (Compound (3))

In 20 ml of DMF (dimethylformamide) were suspended 0.98 g of Compound (1) as synthesized in Reference Example 1, 1.07 g of Compound (2) as synthesized in Reference Example 2, and 0.65 g of 1-hydroxybenzotriazole. Under cooling in an ice/salt bath, 0.88 ml of water-soluble carbodiimide was added thereto and the mixture was stirred at room temperature for 6 hours. Then, 0.28 g of water-soluble carbodiimide hydrochloride was further added thereto and the mixture was stirred overnight. After the solvent was distilled off, the resulting residue was dissolved in water and ethyl acetate and the solution was separated. The ethyl acetate phase was washed with water, 5% aqueous sodium hydrogencarbonate, and water, and dried over anhydrous magnesium sulfate. The solvent was distilled off and the resulting oily residue was purified by silica gel column chromatography (100 ml, ethyl acetate) to obtain 1.10 g of N-(4-t-butoxycarboxamidobutanoyl)-S-(2-pyridylthio)-2-mercaptoethylamine (hereinafter referred to as Compound (3)) (yield 56%). The chemical formula of Compound (3) is shown below.

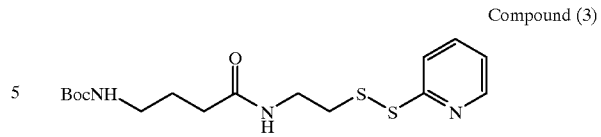

Compound (3)

The NMR data of Compound (3) are as follows.
$^1$H-NMR (400 MHz, CDCl$_3$, ppm) δ 1.44 (9H, s), 1.82 (2H, m, J=7.0 Hz), 2.27 (2H, t, J=7.0 Hz), 2.94 (2H, t, J=6.0 Hz), 3.18 (2H, m), 3.57 (2H, m, J=6.0, 6.0 Hz), 4.86 (1H, s), 7.15 (1H, m, J=1.8, 4.9, 6.7 Hz), 7.39 (1H, s), 7.54 (1H, m, J=0.5, 0.9, 8.1 Hz), 7.63 (1H, m, J=1.8, 4.9, 6.7 Hz), 8.50 (1H, m, J=0.9, 1.8, 4.9 Hz).

REFERENCE EXAMPLE 4

Synthesis of 3,4-di-t-butoxycarboxamidobenzoic acid (Compound (4))

3,4-Diaminobenzoic acid (3.04 g) was dissolved in 25 ml of 1 N aqueous sodium hydroxide and 9.6 g of di-t-butyldicarbonate in 30 ml of acetone was added thereto. The mixture was stirred overnight. Then, 2.0 g of di-t-butyldicarbonate and 5 ml of 1 N aqueous sodium hydroxide were further added thereto and the mixture was stirred for additional 3 days. After acetone was distilled off, water and ethyl acetate were added to the resulting residue and mixed well to separate the solution. The aqueous phase was extracted with ethyl acetate. The ethyl acetate phases were combined and extracted twice with 5% aqueous sodium hydrogencarbonate. All the aqueous phases were combined and ethyl acetate was added thereto. After adjusting pH to about 3 with 6 N hydrochloric acid, the solution was separated. The aqueous phase was extracted twice with ethyl acetate. The ethyl acetate phases were combined and washed with water. The resulting extract was concentrated and crystals deposited were collected by filtration. Crystals were washed with ethyl acetate and dried over diphosphorus pentoxide to obtain 5.55 g of 3,4-di-t-butoxy carboxamidobenzoic acid (hereinafter referred to as Compound (4)) (yield 79%). The chemical formula of Compound (4) is shown below.

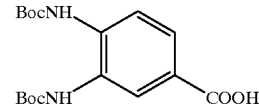

Compound (4)

The NMR data of Compound (4) are as follows.
$^1$H-NMR (400 MHz, DMSO-D$_6$, ppm) δ 1.48 (9H, s), 1.49 (9H, s), 7.63 (1H, d, J=8.6 Hz), 7.71 (1H, d, J=8.6 Hz), 8.09 (1H, s), 8.68 (1H, s), 8.73 (1H, s), 12.6–13.0 (1H, broad s).

REFERENCE EXAMPLE 5

Synthesis of N-succinimide 3,4-di-t-butoxycarboxamidobenzoate (Compound (5))

Compound (4) synthesized in Reference Example 4 (5.50 g) and 2.70 g of N-hydroxysuccinimide were dissolved in 50 ml of DMF. Under cooling with ice, 4.50 g of water-soluble carbodiimide hydrochloride was added thereto and the mixture was stirred. After 2 hours, the temperature was returned to room temperature and the solution was stirred overnight. The solvent was distilled off and the resulting residue was dissolved by adding water and ethyl acetate. Then, the solution was separated. The ethyl acetate phase was washed successively with water, 5% aqueous sodium hydrogencarbonate, 5% aqueous citric acid, and water, and dried over anhydrous magnesium sulfate. The solvent was distilled off and crystallization was conducted from hexane. Crystals were collected by filtration to obtain 6.63 g of N-succinimide 3,4-di-t-butoxycarboxamidebenzoate (hereinafter refereed to as Compound (5)) (yield 95%). The chemical formula of Compound (5) is shown below, in which NSu represents succinimide.

Compound (5)

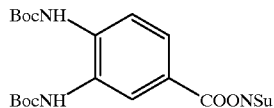

The NMR data of Compound (5) are as follows.

$^1$H-NMR (400 MHz, DMSO-D$_6$, ppm) δ 1.49 (9H, s), 1.50 (9H, s), 2.88 (4H, s), 7.78 (1H, d, J=8.6 Hz), 7.95 (1H, d, J=8.6 Hz), 8.28 (1H, s), 8.89 (1H, s), 8.99 (1H, s).

REFERENCE EXAMPLE 6

Synthesis of N-(4-(3,4-diaminobenzamido)butanoyl)-S-(2-pyridylthio)-2-mercaptoethylamine (Compound (7))

Compound (3) synthesized in accordance with the method as described in Reference Example 3 (1.54 g) was dissolved in 5 ml of chloroform and 5 ml of trifluoroacetic acid was added thereto. The mixture was stirred for 30 minutes at room temperature and the solvent was distilled off. Chloroform was added to the resulting residue and then solvent was distilled off. This procedure was repeated three times and the resulting residue was dissolved in 20 ml of DMF. This was cooled with ice and neutralized with triethylamine. Compound (5) (1.86 g) was added thereto and the mixture was allowed to react overnight while adjusting pH to 7 to 8 with triethylamine. The solvent was distilled off and the resulting residue was dissolved in water and ethyl acetate to separate the solution. The ethyl acetate phase was washed successively with 5% aqueous citric acid, 5% aqueous sodium hydrogencarbonate, and water, and dried over anhydrous magnesium sulfate. The solvent was distilled off to obtain N-(4-(3,4-di-t-butoxycarboxamidobenzamido)butanoyl)-S-(2-pyridylthio)-2-mercaptoethylamine (hereinafter referred to as Compound (6)) as an oil. The chemical formula of Compound (6) is shown below.

Compound (6)

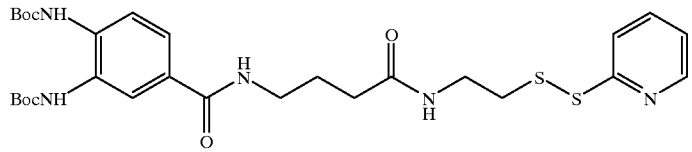

The NMR data of Compound (6) are as follows.

$^1$H-NMR (300 MHz, CDCl$_3$, ppm) δ 1.51 (9H, s), 1.52 (9H, s), 1.97 (2H, m), 2.34 (2H, t, J=6.9 Hz), 2.90 (2H, t, J=5.5 Hz), 3.46–3.57 (4H, m), 6.7–6.9 (1H, broad s), 7.10–7.17 (2H, m), 7.52–7.70 (4H, m), 7.82 (1H, s), 8.47 (1H, d, J=4.9 Hz).

The whole amount of Compound (6) was dissolved in 10 ml of trifluoroacetic acid and the solution was stirred for 1 hour at room temperature. After distilling off trifluoroacetic acid, water was added thereto and distilled off. The resulting residue was dissolved in water, adsorbed to 45 ml of Diaion HP-20 packed in a column, washed with 250 ml of water, and eluted with 300 ml of 40% aqueous acetonitrile. The eluate was collected and concentrated. An oil separated was dissolved in a small amount of acetonitrile and freeze-dried to obtain 1.30 g of N-(4-(3,4-diaminobenzamido)butanoyl)-S-(2-pyridylthio)-2-mercaptoethylamine (hereinafter referred to as Compound (7)). The chemical formula of Compound (7) is shown below.

Compound (7)

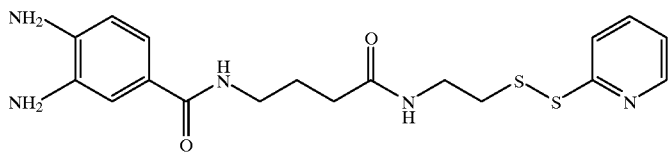

The NMR data of Compound (7) are as follows.

$^1$H-NMR (400 MHz, DMSO-D$_6$, ppm) δ 1.70 (2H, m), 2.10 (2H, t, J=7.3 Hz), 2.89 (2H, t, J=6.8 Hz), 3.18 (2H, m), 3.33 (2H, m), 5.42 (4H, broad s), 6.53 (1H, d, J=8.1 Hz), 7.05 (1H, dd, J=1.9, 8.1 Hz), 7.15 (1H, d, J=1.9 Hz), 7.23 (1H, m, J=1.1, 4.8, 7.3 Hz), 7.76 (1H, m, J=0.9, 1.1, 8.4 Hz), 7.82 (1H, m, J=1.8, 7.3, 8.4 Hz), 7.94 (1H, broad t), 8.06 (1H, broad t), 8.45 (1H, m, J=0.9, 1.8, 4.8 Hz).

EXAMPLE 1
Synthesis of N-(4-(3-(2,3,4-trihydroxybutyl)quinoxaline-6-carboxamido)butanoyl)-S-(2-pyridylthio)-2-mercaptoethylamine (Compound (8-1)) and N-(4-(2-(2,3,4-trihydroxybutyl)quinoxaline-6-carboxamido)butanoyl)-S-(2-pyridylthio)-2-mercaptoethylamine (Compound (8-2))

Compound (7) synthesized in Reference Example 6 (28.95 mg) was dissolved in 1 ml of methanol and was mixed with 1 ml of PBS having dissolved therein 36.92 mg of 3-deoxy-D-erythrohexos-2-ulose (3-deoxyglucosone) (hereinafter referred to as 3-DG) synthesized in accordance with the method as described in Carbohyd. Res. 17, 183–192, 1971. The reaction mixture was stirred overnight at room temperature under argon atmosphere. The reaction mixture was diluted with water, adsorbed to 5 ml of Diaion HP-20 packed in a column, washed with water, and eluted with 40% aqueous acetonitrile. The eluate was concentrated, adsorbed to 7 ml of Diaion HP-20 packed in a column, and eluted serially with 5, 10, and 20% aqueous acetonitrile. Fractions eluted with 20% aqueous acetonitrile were collected, concentrated, and freeze-dried to obtain Compound (8). Compound (8) is a mixture of N-(4-(3-(2,3,4-trihydroxybutyl)quinoxaline-6-carboxamido)butanoyl)-S-(2-pyridylthio)-2-mercaptoethylamine (hereinafter referred to as Compound (8-1)) and N-(4-(2-(2,3,4-trihydroxybutyl)quinoxaline-6-carboxamido)butanoyl)-S-(2-pyridylthio)-2-mercaptoethylamine (hereinafter referred to as Compound (8-2)) and its yield as a mixture of isomers was 26.70 mg. The chemical formulae of Compounds (8-1) and (8-2) are shown below.

The NMR data of Compound (8) are as follows.

$^1$H-NMR (400 MHz, DMSO-D$_6$, ppm) δ 1.81 (2H, m), 2.18 (2H, t, J=7.3 Hz), 2.90 (2H, t, J=6.8 Hz), 3.02 (2H, m), 3.34 (4H, m), 3.45 (2H, m), 3.61 (1H, m), 3.93 (1H, m), 4.45 (1H, broad s), 4.78 (2H, m), 7.22 (1H, m), 7.76 (1H, d, J=8.1 Hz), 7.81 (1H, dd, J=7.2, 8.1 Hz), 8.08 (2H, m), 8.17 (0.4H, d, J=8.8 Hz), 8.21 (0.6H, d, J=8.8 Hz), 8.45 (1H, d, J=4.6 Hz), 8.54 (0.4H, S), 8.56 (0.6 H, s), 8.82 (1H, broad d, J=5.1 Hz), 8.90 (0.4H, s), 8.91 (0.6H, s).

EXAMPLE 2
Synthesis of KLH-bound pyrazine derivatives

A binding product of Compound (8) and keyhole lympet hemocyanin (hereinafter referred to as KLH) (Calbiochem) was synthesized as an immunogen. Namely, 11.16 mg of KLH was dissolved in 893 μl of 0.1 M phosphate buffer (pH 7.5) and 2.23 mg of GMBS (N-succinimidyl 4-maleimide acetate, Dojindo Laboratories) in 223 μl of DMF was added thereto. The solution was stirred for 1 hour at room temperature. A 500 μl each portion of the reaction solution was applied to two PD-10 columns (Pharmacia) each equilibrated with 0.1 M phosphate buffer (pH 7.0) containing 1 mM EDTA and eluted with the same buffer. In both columns, the first 2.5 ml was discarded and the following 2.0 ml was collected.

Separately, 3.46 mg of Compound (8) synthesized in Example 1 was dissolved in 300 μl of 20% aqueous acetonitrile. After adding thereto 11.56 mg of dithiothreitol, the mixture was allowed to stand at room temperature for 30 minutes. A 150 μl portion of the thus-obtained reducing solution was subjected to reversed phase HPLC (YMC-Pack AP-322, internal diameter (I.D.) 10 mm×length (L) 150 mm) and gradient elution was carried out with 0.1 M phosphate buffer (pH 7.0) containing 1 mM EDTA and 10–20% acetonitrile. Peak fractions at the retention time of 10 minutes (A) and 10.8 minutes (B) were independently collected. Each of fractions (A) and (B) was added to a KLH maleimide solution prepared as described above and stirred at room temperature. After 40 minutes, the remaining reducing solution (150 μl) was separated as described above and added to each reaction solution and the reaction was effected for 3 hours. The reaction solutions were transferred to dialysis tubes and dialyzed overnight against PBS to obtain KLH-bound pyrazine derivatives. About 7 ml (346 mg/ml) of KLH-bound pyrazine derivative was obtained from fraction (A) and about 6 ml (375 mg/ml) of KLH-bound pyrazine derivative was obtained from fraction (B).

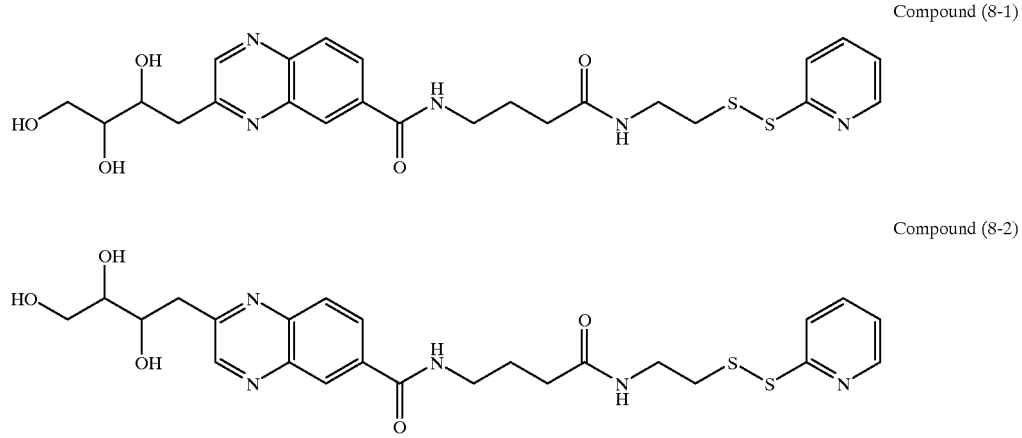

Compound (8-1)

Compound (8-2)

EXAMPLE 3
Synthesis of BSA-bound pyrazine derivatives

Using 12.88 mg of bovine serum albumin (BSA) and 3.3 mg of Compound (8) synthesized in Example 1, a binding product of Compound (8) and BSA was synthesized in the same manner as in Example 2 as an antigen to be used in the immunological assay. As a result, from fractions (A) and (B) obtained by reversed phase HPLC, about 8 ml (590 mg/ml) and about 7 ml (665 mg/ml) of BSA-bound pyrazine derivatives were obtained, respectively.

EXAMPLE 4
Synthesis of biotin-bound pyrazine derivatives (Compound (9))

A binding product of Compound (8) and biotin (hereinafter referred to as Compound (9)) was synthesized as an antigen to be used in the immunological assay. Namely, 21.35 mg of Compound (8) synthesized in accordance with the method as described in Example 1 was dissolved in 2 ml of 0.1 M phosphate buffer (pH 7.0) containing 1 mM EDTA and 0.2 ml of methanol and 40.35 mg of dithiothreitol was added thereto. The solution was stirred at room temperature under argon atmosphere. Then, the solution was subjected to reversed phase HPLC (Asahi Pack ODP-90, 20 mm I.D.×300 mm L, Showa Denko) and gradient elution was carried out with 0.1 M phosphate buffer (pH 7.0) containing 1 mM EDTA and 10–20% acetonitrile. Peak fractions with the retention time of about 26 minutes (A) and about 27 minutes (B) were collected. Biotin-PE-maleimide (Dojindo Laboratories) was added to fraction (A) in an amount of 14.0 mg and to fraction (B) in an amount of 11.3 mg. Each of the solutions was stirred at room temperature under argon atmosphere. The fraction (A) reaction solution was adsorbed to 7 ml of Diaion HP-20 packed in a column, while the fraction (B) reaction solution was adsorbed to 5 ml of Diaion HP-20 packed in a column. After washing each column with 10% aqueous acetonitrile, elution was carried out with 40% acetonitrile and the eluate was freeze-dried to obtain Compound (9). From fractions (A) and (B), 11.35 mg and 4.15 mg of biotin-bound pyrazine derivatives were obtained. The chemical formulae of the thus-obtained derivatives, Compound (9-1) and Compound (9-2), are shown below.

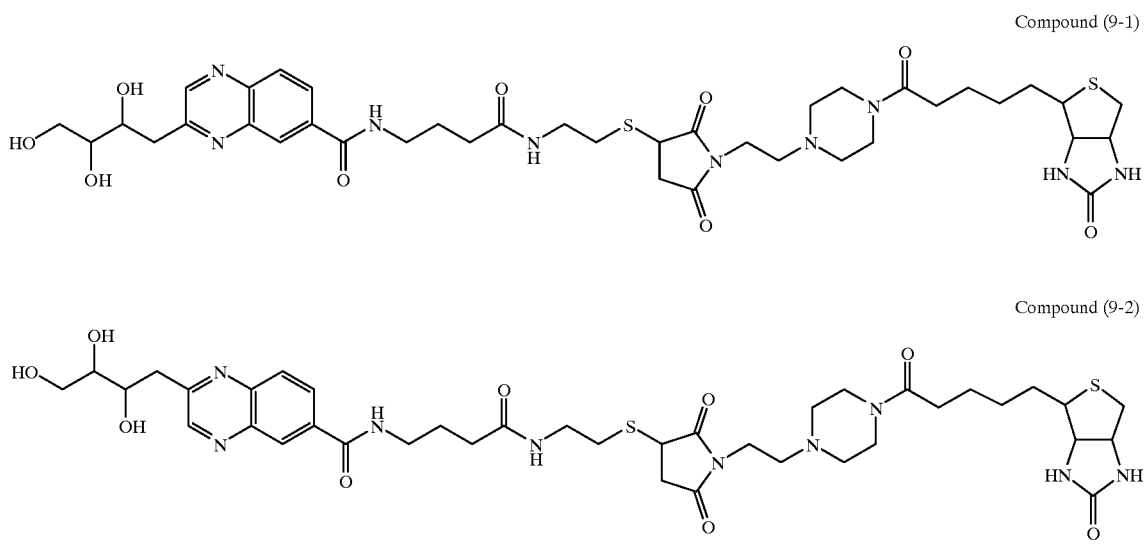

Compound (9-1)

Compound (9-2)

EXAMPLE 5
Synthesis of biotin-bound diaminobenzene derivative (Compound (10))

One hundred mg of Compound (7) synthesized by the method as described in Reference Example 6 was dissolved in 4 ml of 0.1 mM phosphate buffer (pH 7.0) containing 1 mM EDTA and 1 ml of acetonitrile and 115 mg of dithiothreitol was added thereto. The solution was stirred for 1 hour, adsorbed to 10 ml of Diaion HP-20 packed in a column, washed with 50 ml of water, and eluted with 50 ml of 20% aqueous acetonitrile. Biotin-PE-maleimide (42.6 mg) was added to the eluate. The solution was stirred for 5 hours, adsorbed to 20 ml of Diaion HP-20 packed in a column, washed with 50 ml of water, and eluted with 40% aqueous acetonitrile. The eluate was freeze-dried to obtain 53.8 mg of a crude product. This product was purified by reversed phase HPLC to obtain 8.05 mg of Compound (10). The chemical formula of Compound (10) is shown below.

Compound (10)

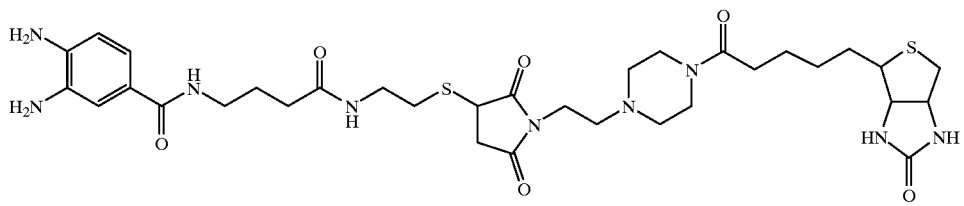

REFERENCE EXAMPLE 7
Synthesis of Nα-(9-fluorenylmethoxycarbonyl)-Nα-(3,4-di-t-butoxycarboxamidobenzoyl-L-lysine (Compound (11))

Nα-(9-fluorenylmethoxycarbonyl)-Nε-t-butoxycarbonyl-L-lysine (0.54 g) was dissolved in 5 ml of chloroform. Five ml of trifluoroacetic acid was added thereto and the solution was stirred at room temperature for 1 hour. The solvent was distilled off and ether was added thereto to form precipitation. The supernatant was removed and the precipitate was dissolved in 5 ml of DMF. Under cooling with ice, 322 μl of triethylamine and 0.67 g of N-succinimidyl 3,4-di-t-butoxycarboxamidobenzoate were added thereto and the solution was stirred overnight at room temperature. The solvent was distilled off and the resulting residue was dissolved in ethyl acetate and dilute hydrochloric acid to separate the solution. The ethyl acetate phase was washed with water and dried over anhydrous magnesium sulfate. The solvent was distilled off and n-hexane was added to the resulting residue. Crystals thus formed were collected by filtration to obtain 0.60 g of Compound (11). The chemical formula of Compound (11) is shown below, in which Fmoc stands for 9-fluorenylmethoxycarbonyl group.

Compound (11)

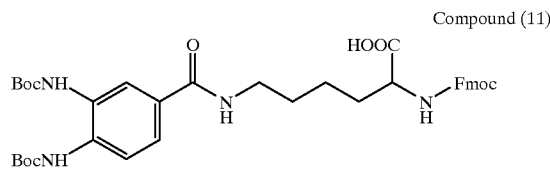

REFERENCE EXAMPLE 8
Synthesis of Nα-(3,4-di-t-butoxycarboxamidebenzoyl)-L-lysine (Compound (12))

Compound (11) synthesized in Reference Example 7 (0.60 g) was dissolved in 7 ml of DMF. Three ml of piperidine was added thereto and the solution was stirred at room temperature for 10 minutes. The reaction solution was poured into 150 ml of 1.5% aqueous trifluoroacetic acid and insoluble matters were removed by filtration. The aqueous phase was passed through 10 ml of Diaion HP-20 packed in a column to adsorb the desired compound. After washing with 50 ml of water, elution was conducted with 100 ml of 40% aqueous acetonitrile. The eluate was concentrated and freeze-dried to obtain 101 mg of Compound (12). The chemical formula of Compound (12) is shown below.

Compound (12)

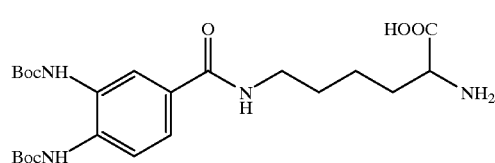

EXAMPLE 6
Synthesis of Nα-(5-(biotinylamino)pentanoyl)-Nε-(3,4-diaminobenzoyl)-L-lysine (compound(13))

Compound (12) synthesized in Reference Example 8 (30.29 mg) was suspended in 3 ml of 0.1 M phosphate buffer (pH 7.5) and DMF solution (10 mg/ml) of biotin-AC5-OSu (Dojindo Laboratories) (4 ml) was added divided into four portions. While vigorously stirring, the solution was stirred overnight at room temperature. The solvent was distilled off and the residue was dissolved in ethyl acetate and water. The solution was made acidic with 6 N hydrochloric acid and crystals deposited were collected by filtration, washed with water, and dried over phosphorus pentoxide. The solid thus obtained was dissolved in 1 ml of trifluoroacetic acid and stirred for 1 hour at room temperature. The solvent was distilled off and the resulting residue was dissolved in water and freeze-dried to obtain 21.14 mg of compound (13). The chemical formula of Compound (13) is shown below.

Compound (13)

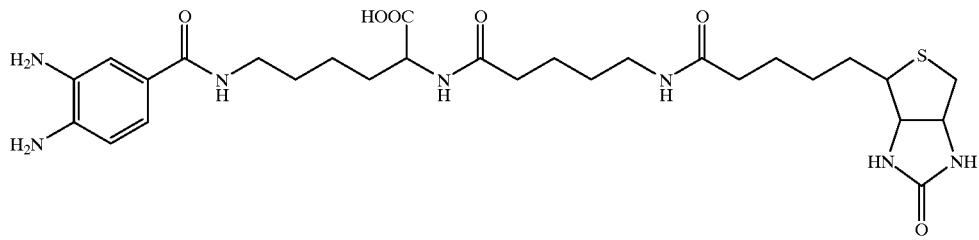

The NMR data of Compound (13) were as shown below.
$^1$H-NMR (400 MHz, DMSO-D$_6$, ppm) δ 1.2–1.8 (16H, m), 2.05 (2H, t, J=7.4 Hz), 2.10 (2H, t, J=7.3 Hz), 2.58 (1H, d, J=12.4 Hz), 2.82 (1H, dd, J=5.1, 12.4 Hz), 3.00 (2H, m), 3.09 (1H, m), 3.19 (2H, m), 3.2–4.0 (4H, broad s), 4.14 (2H, m), 4.31 (1H, m), 6.36 (1H, broad s), 6.42 (1H, broad s), 6.71 (1H, d, J=8.4 Hz), 7.34 (1H, dd, J=0.7, 8.4 Hz), 7.44 (1H, s), 7.72 (1H, m), 8.00 (1H, m), 8.10 (1H, m).

REFERENCE EXAMPLE 9
Synthesis of Nα-biotinyl-Nε-(3,4-diaminobenzoyl)-L-lysine (Compound (14))

Compound (12) synthesized in Reference Example 8 (41.07 mg) was suspended in 4 ml of 0.1 M phosphate buffer (pH 7.5). Three ml of a DMF solution (10 mg/ml) of biotin-OSu (Dojindo Laboratories) was added thereto while vigorously stirring and the mixture was stirred overnight at room temperature. The solvent was distilled off and the resulting residue was dissolved in ethyl acetate and water. The solution was made acidic with 6 N hydrochloric acid and was separated. The ethyl acetate phase was washed with water. After distilling the solvent off, the resulting residue was dissolved in 1 ml of trifluoroacetic acid and stirred for 1 hour at room temperature. The solvent was distilled off and the resulting residue was dissolved in water and acetonitrile and freeze dried to obtain 47 mg of Compound (14). The chemical formula of Compound (14) is shown below.

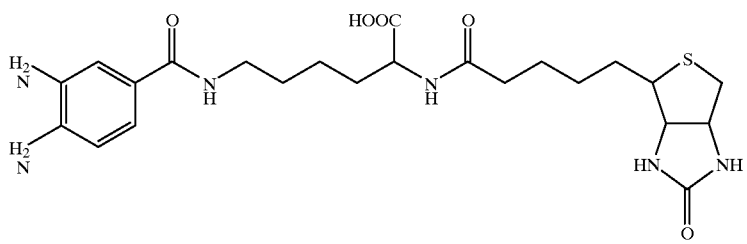

Compund (14)

EXAMPLE 7
Synthesis of anti-pyrazine derivative monoclonal antibody

Anti-pyrazine derivative monoclonal antibody were made by immunizing a BALB/C mouse with the KLH-bound pyrazine derivative derived from fraction (A) synthesized in Example 2 and by fusing spleen lymphocytes of the animal with myeloma cells. Namely, priming of a BALB/C mouse was conducted by using the KLH-bound pyrazine derivative (25–100 μg) emulsified with Freund's complete adjuvant. Two to three weeks later booster immunization was conducted using the same antigen (25–100 μg) emulsified with Freund's incomplete adjuvant. Elevation of the antibody titer was confirmed in the same manner as in a screening method as described later by ELISA using the BSA-bound pyrazine derivative derived from fraction (A) synthesized in Example 3 as a solid phase antigen. After confirming elevation of the antigen titer, KLH-bound pyrazine derivative (25–100 μg) was administered intravenously to the mouse. Three to four days later spleen was excised from the mouse and spleen cells were prepared. Murinemyeloma cells (P3U1) cultured in advance in RPMI-1640 medium were mixed with the spleen cells at a mixing ratio of 1:2–1:5 and cell fusion was effected using polyethylene glycol (Boehringer). Fused cells were suspended in HAT culture medium, distributed into a 96-well culture plate, and cultured at 37° C. in a carbon dioxide incubator.

Screening was conducted using solid phase antigen ELISA. Namely, the BSA-bound pyrazine derivative derived from fraction (A) synthesized in Example 3 were distributed into a 96-well ELISA plate (Pharmacia) in a 50 μl portion per well at a concentration of 1 μg/ml and were allowed to stand overnight at 4° C. for adsorption. After blocking the plate with 1% skim milk, the plate was washed three times with a phosphate buffer containing 0.05% Tween 20 (hereinafter referred to as a washing buffer). Fifty μl of the supernatant of the culture medium used for cell fusion was added to the plate and allowed the reaction to proceed at 37° C. for 1 hour. After similarly washing with the washing buffer three times, an anti-mouse immunoglobulin antibody (Dako) labeled with peroxidase (hereinafter referred to as POD) was added to the plate and the reaction was effected for another 1 hour at 37° C. After washing with the washing buffer four times, ABTS was added thereto as a substrate and wells that developed color were selected. The wells that showed reactivity with the BSA-bound pyrazine derivative were subjected to an inhibition test using a free pyrazine derivative to examine the specificity. Namely, the reaction between a solid phase antigen and the culture supernatant was carried out in the presence of a predetermined concentration (about 10 μM) of the pyrazine derivative and the specificity was confirmed based on whether the reaction was inhibited or not. In this test, the wells in which the reaction was inhibited are regarded as specific to the antigen. Cells in the wells confirmed to be specific were cloned using the limiting dilution method. After culturing in a large scale, cells producing anti-pyrazine derivative monoclonal antibody were administered intraperitoneally to a mouse and ascites containing anti-pyrazine derivative monoclonal antibody was collected. Using protein A-Sepharose, the antibody was purified from ascites to obtain the desired monoclonal antibody. The thus-obtained anti-pyrazine derivative monoclonal antibody was named 3DG-451 antibody and hybridoma producing 3DG-451 antibody has been deposited at National Institute of Bioscience and Human-Technology, Agency of Industrial Science and Technology, of 1–3, Higashi 1-chome, Tsukuba-shi, Ibaraki 305-8566 Japan, since Apr. 1, 1997 under accession number of FERM BP-6346 in accordance with the Budapest Treaty.

EXAMPLE 8
Confirmation of specificity of anti-pyrazine derivative monoclonal antibody Specificity of anti-pyrazine derivative monoclonal antibody was confirmed with the inhibition test based on ELISA using the BSA-bound pyrazine derivative as a solid phase antigen. Namely, BSA-bound pyrazine derivative derived from fraction (A) or (B) synthesized in Example 3 (1 μg/ml) were distributed onto the Nunc ELISA plate (Maxisorp) in 75 μl/well and allowed to stand overnight at 4° C. for adsorption. The plates for adsorption of the BSA-bound pyrazine derivatives derived from fraction (A) and fraction (B) were designated as plate (A) and plate (B), respectively.

Figure 2:
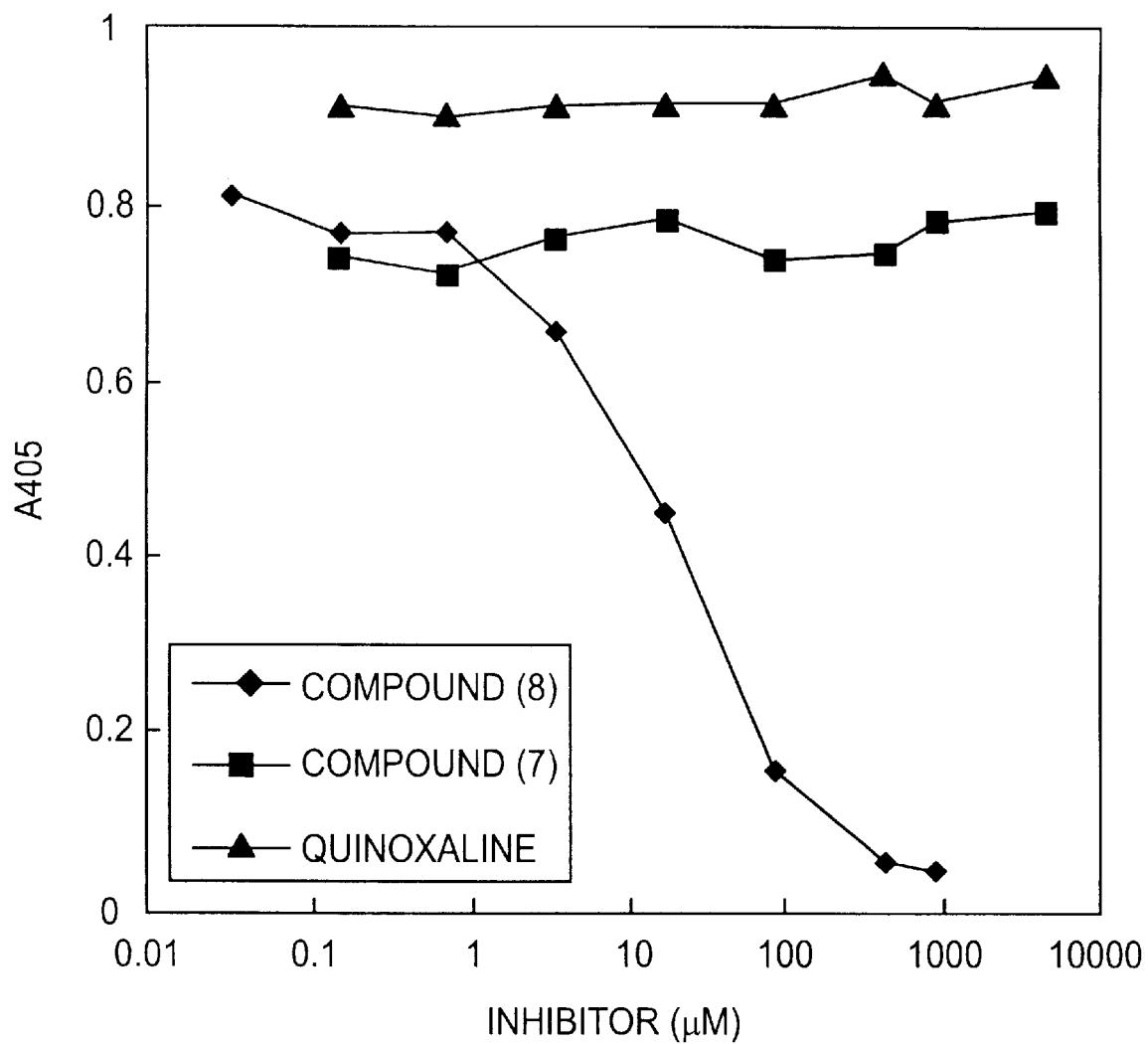
FIG. 2 illustrates the reaction specificity of anti-pyrazine derivative monoclonal antibody 3DG-451 to BSA-bound pyrazine derivatives derived from fraction (B) (plate B) obtained in Example 3.

For blocking, plates (A) and (B) was allowed to stand with 1% skim milk at 37° C. for 3 hours. A solution of the pyrazine derivative (Compound (8)) synthesized in Example 1 diluted by 5 n from 1 mM, the diaminobenzene derivative (Compound (7)) synthesized in Reference Example 6 diluted by 5 n from 10 mM, and quinoxaline (Tokyo Chemical Industry) diluted by 5 n from 10 mM were added to each well (40 μl each) as inhibitors. Then, 40 μl of 3DG-451 antibody (1 μg/ml) was added to each well and allowed to react at 37° C. for 1 hour. After thoroughly washing with the washing buffer, anti-mouse immunoglobulin antibody labeled with POD (Dako) was added to each well and the reaction was allowed to proceed at 37° C. for 1 hour. After thoroughly washing with the washing buffer similarly, ABTS was added to each well as a substrate and the plates were allowed to stand at room temperature for 20–30 minutes. Absorbance at 405 nm was measured with a spectrophotometer. As shown in FIGS. 1 and 2, the reaction between the BSA-bound pyrazine derivatives and 3DG-451 antibody was inhibited by the pyrazine derivative (Compound (8)), but not inhibited at all by the diaminobenzene derivative (Compound (7)) and quinoxaline. Cross-reactivities of 3DG-451 antibody with the diaminobenzene derivative (Compound (7)) and quinoxaline were not more than 0.1%. Thus, the reaction was confirmed to be specific to the pyrazine derivative (Compound (8)).

EXAMPLE 9

Assay of biotin-bound pyrazine derivative (Compound (9))

Figure 3:
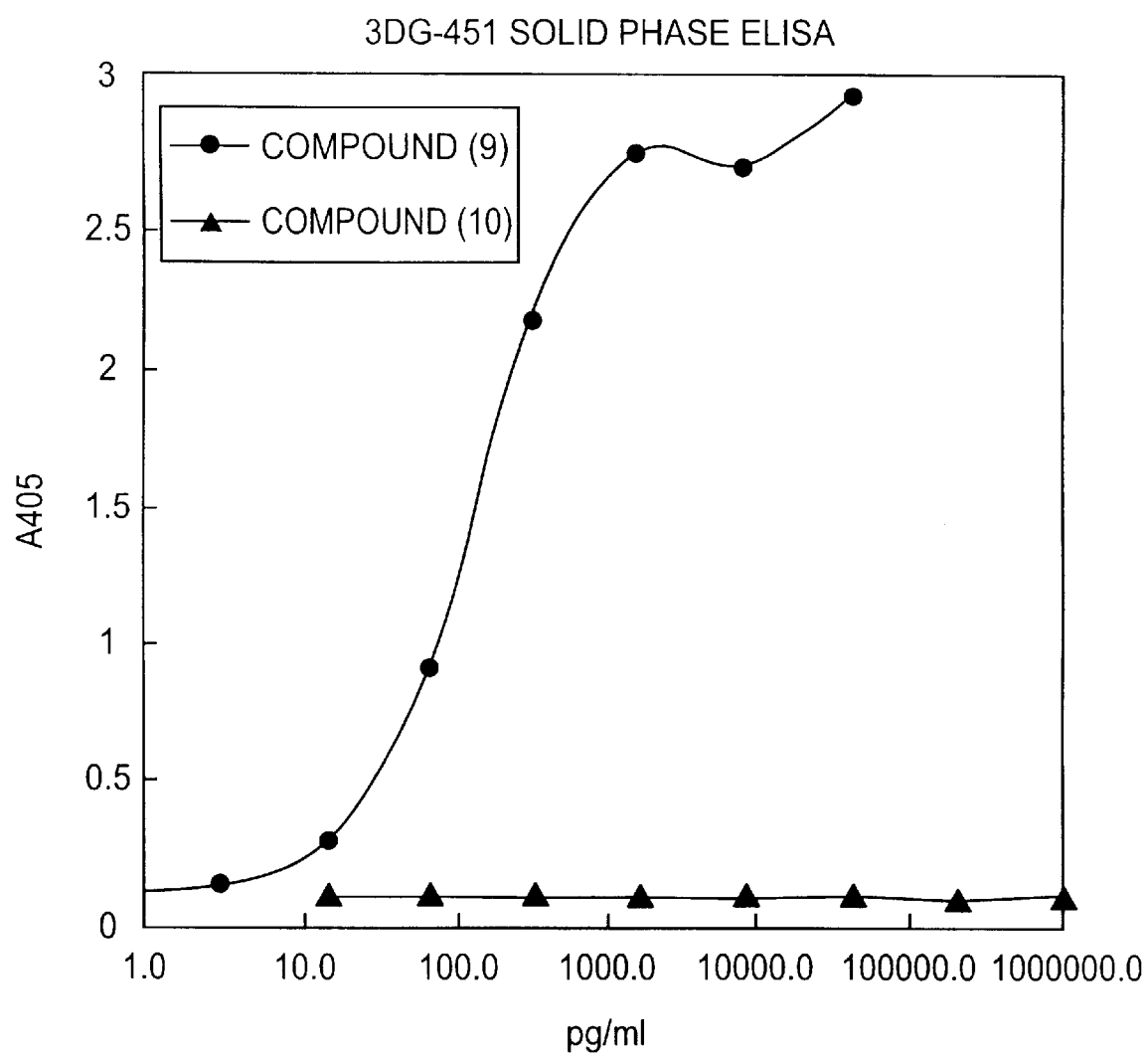
FIG. 3 illustrates the results of measurement of biotin-bound pyrazine derivatives by solid phase ELISA using anti-pyrazine derivative monoclonal antibody 3DG-451.

Compound (9) synthesized in Example 4 was assayed by sandwich ELISA method. A 75 μl portion of 3DG-451 antibody (10 μg/ml) was distributed onto the Nunc ELISA plate (Maxisorp) to each well and allowed to stand overnight at 4° C. for adsorption. For blocking the plate was allowed to stand at 37° C. for 3 hours with 1% skim milk. The biotin-bound pyrazine derivative (Compound (9)) synthesized in Example 4 was diluted by 5 n from 40 ng/ml with tris buffer containing 1% BSA. Each diluted solution was distributed onto the plate for antibody adsorption (75 μl/well) and was allowed to react at 37° C. for 1 hour. Similarly, the biotin-bound diaminobenzene derivative synthesized in Example 5 (Compound (10)) diluted by 5 n from 1000 ng/ml was measured. After completion of the reaction, the plate was washed thoroughly with the washing buffer, a 75 μl portion of avidin labeled with alkaline phosphatase (hereinafter referred to as ALP) (Dako) was added to each well and the reaction was allowed to proceed at 37° C. for another 1 hour. After thoroughly washing with the washing buffer, pNPP was added as a substrate to each well (75 μl/well) and allowed to stand at room temperature for 30 minutes. Then, absorbance at 405 nm was measured. The results are shown in FIG. 3. As shown in FIG. 3, solid phase antibody 3DG-451 did not react with the diaminobenzene derivative (Compound (10)) at all, while the pyrazine derivative (Compound (9)) could be measured at the level of at lowest 10 μg/ml.

EXAMPLE 10

Measurement of 3-deoxyglucosone (3-DG) I

Figure 4:
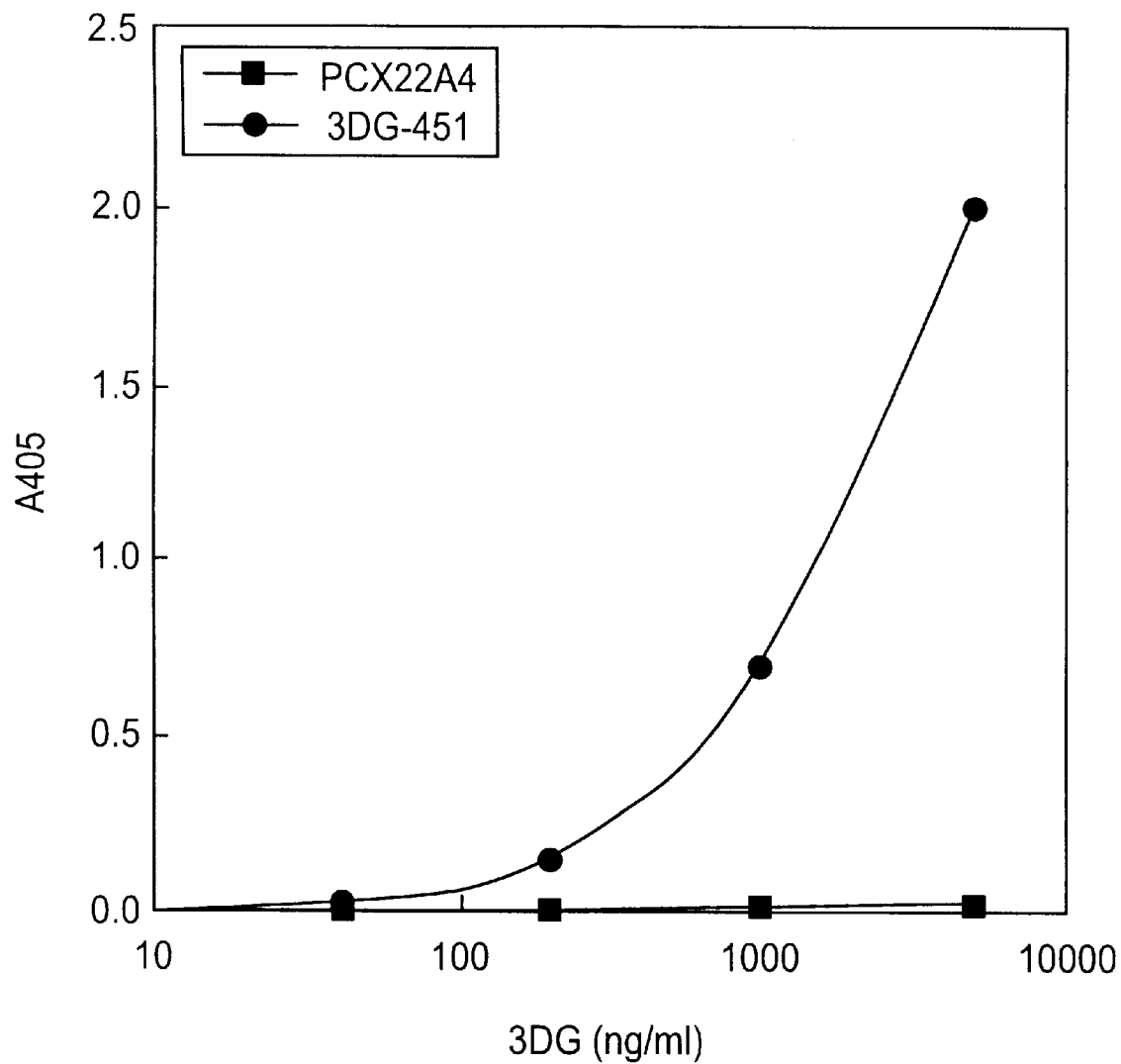
FIG. 4 illustrates the results of measurement of 3-deoxyglucosone by measuring compound (10), which is a reaction product of 3-deoxyglucosone and a diaminobenzene derivative, using anti-pyrazine derivative monoclonal antibody.

3-DG and the biotin-bound diaminobenzene derivative (Compound (10)) synthesized in Example 5 were reacted in PBS overnight at room temperature and the reaction product was measured by solid phase 3DG-451 ELISA. Namely, a solution of the biotin-bound diaminobenzene derivative (Compound (10)) was added to 3-DG diluted by 5 n from 5 μg/ml to a final concentration of 10 μg/ml and allowed to react overnight at room temperature. A 75 μl portion of 3DG-451 antibody (10 μg/ml) was distributed into each well of the Nunc ELISA plate (Maxisorp) and allowed to stand overnight at 4° C. for adsorption. The ELISA plate was blocked with 1% skim milk to serve as an ELISA plate. As control, an ELISA plate was prepared on which monoclonal antibody PCX22A4 with no specificity to the pyrazine derivative was adsorbed. The biotin-bound pyrazine derivative, which is the reaction product of 3-DG and the biotin-bound diaminobenzene derivative (Compound (10)) were measured by ELISA in the same manner as in Example 9 using two kinds of the plates. The results are shown in FIG. 4. As shown in FIG. 4, it was confirmed that 3-DG could be measured by the method of the present invention.

EXAMPLE 11

Measurement of 3-DG II

Figure 5:
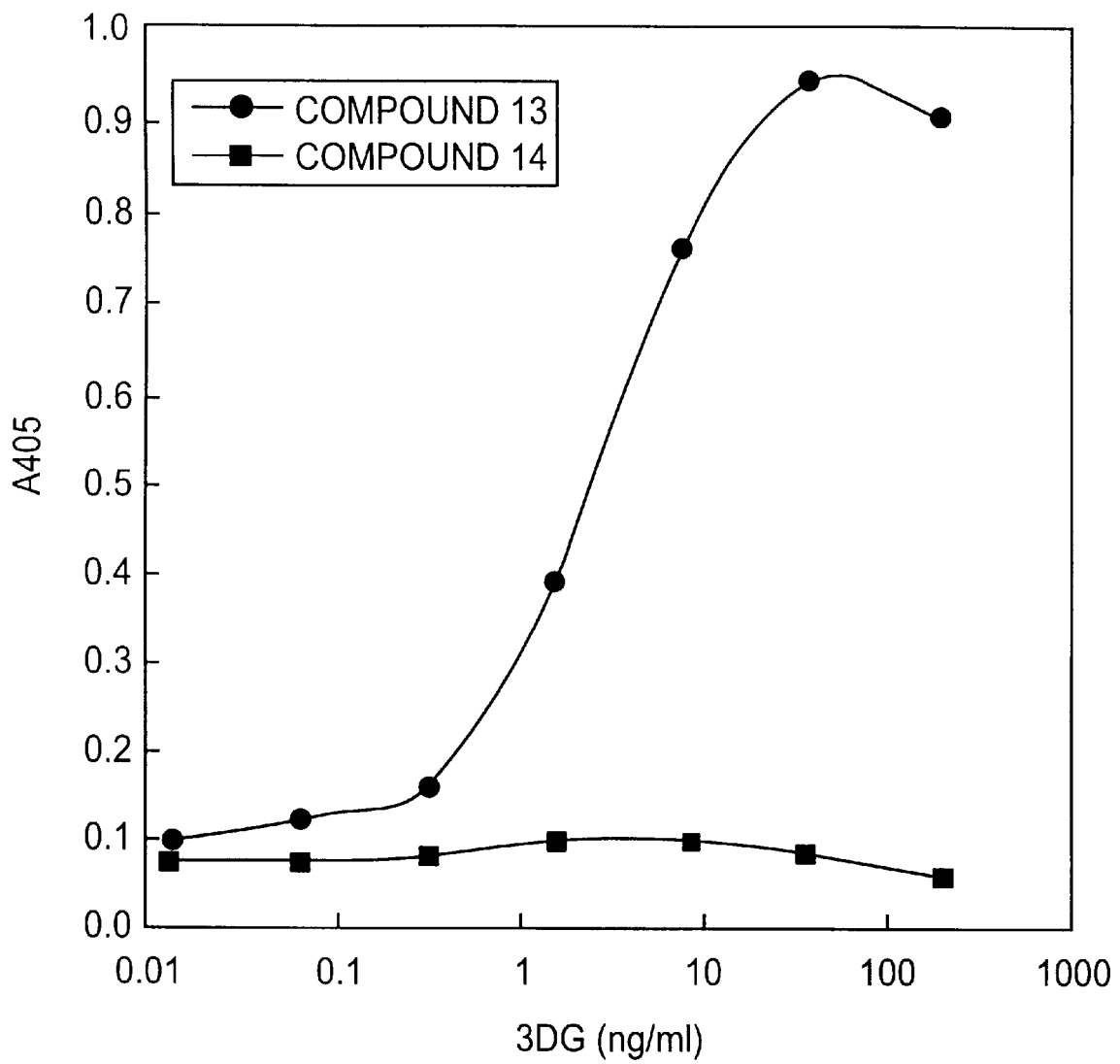
FIG. 5 illustrates the results of measurement of 3-deoxyglucosone by measuring compounds (13) and (14) using anti- pyrazine derivative monoclonal antibody.

3-DG and the biotin-bound diaminobenzene derivative synthesized in Example 6 (Compound (13)) or the biotin-bound diaminobenzene derivative synthesized in Reference Example 9 (Compound (14)) were reacted in PBS overnight at room temperature. The reaction product was measured with solid phase 3DG-451 ELISA. Namely, as in Example 10, Compound (13) or (14) was added to 3-DG diluted by 3 n from 200 ng/ml to a final concentration of 10 μg/ml and allowed to react overnight at room temperature. ELISA was conducted in the same manner as in Example 10. The results are shown in FIG. 5. As shown in FIG. 5, the biotin-bound diaminobenzene derivative (Compound (14)) did not react with the antibody, while the biotin-bound diaminobenzene derivative (Compound (13)) could be measured at the level of at lowest about 100 μg/ml.

What is claimed is:

1. An antibody that recognizes at least a region comprising $R^1$, $R^2$, carbon atoms in the pyrazine ring to which $R^1$ and $R^2$ are respectively attached, and nitrogen atoms in the pyrazine ring attached to said carbon atoms, of a pyrazine derivative represented by the formula (I):

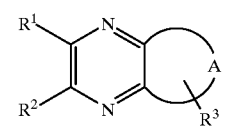

(I)

wherein $R^1$ and $R^2$ independently represent a hydrogen atom, a methyl group, a hydroxymethyl group, a hydroxyethyl group, a dihydroxyethyl group, a dihydroxypropyl group, a trihydroxypropyl group, or a trihydroxybutyl group, A represents a group that binds to the pyrazine ring to form a 6-membered aromatic hydrocarbon group, a 5- or 6-membered aromatic heterocyclic group, or a 5- or 6-membered alicyclic hydrocarbon group, wherein $R^3$ represents a linking residue, and wherein said 5-membered ring formed by A may have 1 or 2 substituents and said 6-membered ring may have 1 to 3 substituents, in addition to $R^3$.

2. The antibody according to claim 1, wherein $R^1$ and $R^2$ represent (1) a hydrogen atom and a trihydroxybutyl group, respectively; (2) a methyl group and a trihydroxypropyl group, respectively; or (3) a hydroxymethyl group and a dihydroxypropyl group, respectively.

3. The antibody according to claim 1, wherein $R^1$ represents a hydrogen atom and $R^2$ represents a methyl group.

4. The antibody according to claim 1, wherein said ring formed by A represents pyridine, benzene, furan, or thiophene.

5. The antibody according to claim 2, wherein said ring formed by A represents pyridine, benzene, furan, or thiophene.

6. The antibody according to claim 3, wherein said ring formed by A represents pyridine, benzene, furan, or thiophene.

7. The antibody according to claim 4, wherein $R^3$ comprises a reactive residue and a spacer residue.

8. The antibody according to claim 5, wherein $R^3$ comprises a reactive residue and a spacer residue.

9. The antibody according to claim 6, wherein $R^3$ comprises a reactive residue and a spacer residue.

10. The antibody according to claim 7, wherein said reactive residue represents a carboxyl group, a hydroxyl group, a sulfhydryl group, an amino group, a maleimide group, an aldehyde group, a halogen atom, or derivatives thereof capable of reacting with a compound to form a covalent bond.

11. The antibody according to claim 8, wherein said reactive residue represents a carboxyl group, a hydroxyl group, a sulfhydryl group, an amino group, a maleimide group, an aldehyde group, a halogen atom, or derivatives thereof capable of reacting with a compound to form a covalent bond.

12. The antibody according to claim 9, wherein said reactive residue represents a carboxyl group, a hydroxyl group, a sulfhydryl group, an amino group, a maleimide group, an aldehyde group, a halogen atom, or derivatives thereof capable of reacting with a compound to form a covalent bond.

13. The antibody according to claim 7, wherein said spacer residue represents an aliphatic hydrocarbon group, an aromatic hydrocarbon group, or these groups bound to each other via an ester bond, an amide bond, an ether bond, a thioether bond, a disulfide bond, or a Schiff base bond.

14. The antibody according to claim 8, wherein said spacer residue represents an aliphatic hydrocarbon group, an aromatic hydrocarbon group, or these groups bound to each other via an ester bond, an amide bond, an ether bond, a thioether bond, a disulfide bond, or a Schiff base bond.

15. The antibody according to claim 9, wherein said spacer residue represents an aliphatic hydrocarbon group, an aromatic hydrocarbon group, or these groups bound to each other via an ester bond, an amide bond, an ether bond, a thioether bond, a disulfide bond, or a Schiff base bond.

16. The antibody according to claim 1, wherein one of $R^1$ and $R^2$ represents a hydrogen atom and the other represents a 2,3,4-trihydroxybutyl group, the ring formed by A represents benzene, and $R^3$ represents a 4-carboxamidobutanoyl-(2-mercapto) ethylamide group.

17. The antibody according to claim 1, which is a monoclonal antibody.

18. The antibody according to claim 4, which is a monoclonal antibody.

19. The antibody according to claim 5, which is a monoclonal antibody.

20. The antibody according to claim 6, which is a monoclonal antibody.

21. The antibody according to claim 16, which is a monoclonal antibody.

22. The antibody according to claim 16, which is monoclonal antibody 3DG-451 produced by hybridoma deposited under accession number FERM BP-6346.

23. A method for immunological determination of a 1,2-dicarbonyl derivative, which comprises the steps of:

reacting a 1,2-dicarbonyl derivative in a specimen with a diamino derivative represented by the formula (II):

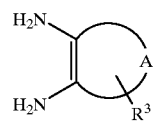

(II)

wherein $R^3$ and A are as defined in the formula (I) of claim 1, to produce the pyrazine derivative of the formula (I); and measuring said pyrazine derivative by an immunological method utilizing an antigen-antibody reaction between said pyrazine derivative and the antibody according to any one of claims 1 to 10 to thereby determine the 1,2-dicarbonyl derivative in the specimen.

24. The method according to claim 23, wherein $R^3$ of the diamino derivative of formula (II) is labeled with a detectable label and said immunological method comprises binding said antibody to a solid phase, reacting said antibody bound to the solid phase with said pyrazine derivative, washing it, and determining the amount of the label bound to the solid phase.

25. The method according to claim 24, wherein said label is biotin.

26. The method according to claims 23, wherein said 1,2-dicarbonyl derivative is deoxyglucosone.

27. The method according to claims 23, wherein said 1,2-dicarbonyl derivative is methylglyoxal.

28. A kit for immunological determination of a 1,2-dicarbonyl derivative comprising:

an antibody that recognizes at least a region comprising $R^1$, $R^2$, carbon atoms in the pyrazine ring to which $R^1$ and $R^2$ respectively attached, and nitrogen atoms in the pyrazine ring attached to said carbon atoms, of a pyrazine derivative represented by the formula (I):

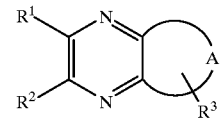

(I)

wherein $R^1$ and $R^2$ independently represent a hydrogen atom, a methyl group, a hydroxymethyl group, a hydroxyethyl group, a dihydroxyethyl group, a dihydroxypropyl group, a trihydroxypropyl group, or a trihydroxybutyl group, A represents a group that binds to the pyrazine ring to form a 6-membered aromatic hydrocarbon group, a 5- or 6-membered aromatic heterocyclic group, or a 5- or 6-membered alicyclic hydrocarbon group, wherein $R^3$ represents a linking residue, and wherein said 5-membered ring formed by A may have 1 or 2 substituents and said 6-membered ring may have 1 to 3 substituents, in addition to $R^3$; and

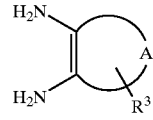

(II)

a diamino derivative represented by the formula (II): where $R^3$ and A are as defined in the formula (I).

29. The kit according to claim 28, wherein said antibody is immobilized.

30. The kit according to claim 28, further comprising a carrier for immobilization of the antibody.

31. The kit according to claim 28, wherein the diamino derivative is labeled.

32. The kit according to claim 28, further comprising a substance for labeling the diamino derivative.

* * * * *